(12) United States Patent
Bourdon et al.

(10) Patent No.: US 6,844,472 B1
(45) Date of Patent: Jan. 18, 2005

(54) METHOD AND INSTALLATION FOR SEPARATING AND PURIFYING DIPHENOLS IN THE PHENOL AND PHENOL DERIVATIVES INDUSTRY

(75) Inventors: Jacques Bourdon, Sainte Foy les Lyon (FR); Daniel Clerin, Saint Genis Laval (FR)

(73) Assignee: Rhodia Chimie, Boulogne Billancourt (FR)

( * ) Notice: Subject to any disclaimer, the term of this patent is extended or adjusted under 35 U.S.C. 154(b) by 0 days.

(21) Appl. No.: 09/889,957

(22) PCT Filed: Jan. 25, 2000

(86) PCT No.: PCT/FR00/00166

§ 371 (c)(1),
(2), (4) Date: Dec. 5, 2001

(87) PCT Pub. No.: WO00/43334

PCT Pub. Date: Jul. 27, 2000

(30) Foreign Application Priority Data

Jan. 25, 1999 (FR) .......................................... 99 00908

(51) Int. Cl.⁷ ......................... C07C 37/68; C07C 37/70; C07C 37/72; C07C 37/74; C07C 37/80
(52) U.S. Cl. ..................... 568/758; 568/716; 568/731; 568/749; 568/751; 568/752; 568/753; 568/763
(58) Field of Search ................................. 568/763, 716, 568/731, 749, 750, 751, 752, 753

(56) References Cited

U.S. PATENT DOCUMENTS 3,969,420 A * 7/1976 Suda et al. .................. 568/751
4,308,110 A * 12/1981 Hosaka et al. ................ 203/48

FOREIGN PATENT DOCUMENTS

FR         2 467 185         4/1981

\* cited by examiner

*Primary Examiner*—Elvis O. Price
(74) *Attorney, Agent, or Firm*—Burns, Doane, Swecker & Mathis, L.L.P.

(57) ABSTRACT

A method and installation for separating and purifying a crude mixture containing hydroquinone, resorcinol and possibly tars and/or catechol, comprising the following steps: —a possible distillation stage (I) in order to obtain a catechol head, —the foot (I) or crude mixture undergoes distillation (II) in order to obtain a fraction that is rich in resorcinol, —the foot of (II) undergoes distillation (III) in order to obtain a fraction that is rich in hydroquinone, whereupon said rich fractions are refined (IV or V). Preferably, one or several stages in which tar is removed (I,I') precede stage (I) or (II).

31 Claims, 2 Drawing Sheets

METHOD AND INSTALLATION FOR SEPARATING AND PURIFYING DIPHENOLS IN THE PHENOL AND PHENOL DERIVATIVES INDUSTRY

The present invention relates to a process for the separation and purification of crude mixtures essentially comprising hydroquinone and resorcinol, optionally tars and optionally catechol, in order to extract therefrom first the hydroquinone and secondly the resorcinol, and the catechol, when it is present, and optionally to purify these various compounds. It also relates to the plants which allow this process to be implemented.

The phenol and phenol derivatives industry generates large volumes of byproducts comprising, among a great variety of tars, the para, ortho and meta derivatives of dihydroxybenzene. They are hydrocuinone (para compound: 1,4-dihydroxybenzene), catechol or pyrocatechin (ortho compound: 1,2-dihydroxybenzene) and resorcinol or resorcin (meta compound: 1,3-dihydroxybenzene).

These three compounds have an added value but their extraction from such complex mixtures is not without presenting problems of a technical nature and an economic nature. Moreover, hydroquinone and resorcinol are isomers which are particularly difficult to separate.

FR-A-2 467 185 discloses a process for the separation and purification of resorcinol and hydroquinone involving stages of distillation and of recrystallization by using a solvent such as water or an organic solvent. According to one alternative form, this process provides distillation stages using steam for entraining the hydroquinone in the form of hydroquinone vapor. This process uses a third solvent which subsequently has to be removed, which requires additional stages and devices, for example for filtration and for drying, and optionally for reprocessing or recycling the solvent.

An object of the present invention, which relates in particular to the separation and the purification of diphenols in the phenol and phenol derivatives industry, is to provide an appropriate method and plant which make it possible to separate and to purify, under favorable economical conditions, hydroquinone and resorcinol from a crude mixture.

Another object of the invention is to make possible the separation and the purification of first hydroquinone and secondly resorcinol from a crude mixture comprising other compounds, in particular tars, and/or optionally catechol, and also to separate and purify the catechol optionally present.

Another object of the invention is to provide such a process which can be operated largely continuously.

Yet another object of the invention is to provide such a process and plant which make it possible to obtain hydroquinone, resorcinol and catechol having a high purity, in particular of greater than 98%, preferably than 99%, indeed even greater than or equal to 99.5%.

Yet another object of the invention is to provide such a process which does not require the use of a third solvent.

These objects are achieved in accordance with the invention by a process for the purification of a crude mixture comprising hydroquinone and resorcinol, optionally tars, and optionally catechol, in which process the crude mixture is subjected to a series of distillation stages, preferably carried out continuously, comprising:
  (i) an optional first distillation stage (I) designed to produce catechol as distillation top product; this stage is carried out when the crude mixture comprises catechol, in particular when the content of catechol in the crude mixture exceeds 2% inclusive,
  (ii) the distillation bottom product obtained under (i) where the crude mixture in the absence of stage (I) is subjected to a distillation stage (II) designed to produce, as distillation top product, a resorcinol-rich fraction comprising resorcinol, essentially, and hydroquinone,
  (iii) the distillation bottom product obtained under (ii) is subjected to a distillation stage (III) designed to produce, as distillation top product, a hydroquinone-rich fraction comprising hydroquinone, essentially, and resorcinol, and then the hydroquinone-rich fraction and/or the resorcinol-rich fraction is/are subjected to a refining stage (IV, V) in order to extract the hydroquinone and/or the resorcinol.

In order to improve the yield for the recovery of hydroquinone from the crude mixture, it is preferable to precede stages (I) and/or (II) by at least one predistillation "detarring" stage (1) which makes it possible to remove the tars as distillation bottom product. It is even preferable then to redistil this distillation bottom product in at least one second preliminary detarring stage (1') and to recover the distillation top product, capable of comprising a certain amount of the desired compounds. The distillation [lacuna] or the two (or more) distillation top products thus obtained are conveyed as feed mixture to stage (I), if such a stage is provided, or stage (II), in the contrary case. More preferably, these preliminary stages are carried out continuously with the distillation stages which follow.

The mixtures to which the process applies are mainly those comprising in particular, with respect to the total mixture:
  from 20 to 60%, in particular from 30 to 50%, by weight of hydroquinone,
  from 2 to 20%, in particular from 2 to 15%, by weight of resorcinol,
  from 0 to 20%, in particular from 5 to 15%, by weight of catechol,
  the remainder being formed of various compounds, essentially tars.

The "detarring" distillation stages (1, 1') can be carried out with scraped falling film devices of conventional design or short path devices. However, the use of multistage columns is not ruled out (see, e.g., column (III)). The aim is simply to remove as much as possible of the tars without a significant loss of the desired compounds.

If stages (1 and 1') are not provided, it is preferable to use columns (I) and (II) with antifouling packings in order to limit the fouling thereof by the tars. Such packings are fully known to a person skilled in the art.

Stage (I) is targeted simply at extracting the catechol and thus at obtaining, as top product, catechol with a purity which is as high as possible. The aim in particular is to obtain a fraction comprising at least 98%, preferably at least 99%, of catechol.

The term "rich" as used above for stages (II) and (III) is understood to mean that the compound targeted is the major component, the other compound being a minor component but present in a sufficient amount to subsequently make possible the refining. A person skilled in the art is entirely in a position to determine by routine tests the ranges of ratios, basing himself on the crystallization curve of a resorcinol/hydroquinone mixture, in order to determine the ratios corresponding to the range of the eutectics. From this information, by varying the operating parameters of the columns, it is possible to achieve conditions such that the rich fractions have a ratio which appears on either side of this range, as is known per se, which will allow the subsequent implementation of the refining.

The operating conditions of stages (II) and (III) are thus related. Each is targeted at the production, as distillation top product (as column top product), of a hydroquinone/resorcinol mixture which is compatible with the subsequent refining stage.

It is thus preferable for stage (III) to result in a mixture comprising:

from 75 to 95%, preferably from 85 to 92%, of resorcinol, from 5 to 25%, preferably from 8 to 15%, of hydroquinone.

(Possible residues of other compounds, e.g. catechol, which remain minor components, are not taken into account).

These operating conditions make it possible to ensure, during stage (III), the production as distillation top product of a mixture comprising in particular:

from 75 to 98%, preferably from 85 to 97.5%, of hydroquinone, from 2 to 25%, preferably from 2.5 to 15%, of resorcinol.

(Here again, possible residues of other compounds which may be present in negligible amounts are not taken into account).

From this information, a person skilled in the art is fully in a position to choose the means to be employed according to the starting mixture. The following should simply be noted. The size (in particular the diameter) of the distillation columns depends on the circulating stream and on the internal pressure. They will thus be dimensioned mainly according to the flow rate of the mixture to be treated. The internal parameter which is the number of theoretical stages is determined in particular by the composition (ratios) of the entering mixture and the purity or the composition of the mixture which has to be obtained as distillation top product and as distillation bottom product. It will be specified that the columns may without distinction be packed with plates or with stacked packing, as is fully known to a person skilled in the art. The plant having been determined, a person skilled in the art adjusts the operating parameters of the columns.

Thus, the distillation column (I) can advantageously but not limitingly be a column having the following specifications:

number of theoretical stages: from 5 to 40, preferably from 10 to 30;

reflux ratio R of between 1 and 10, preferably between 2 and 5.

The distillation column (II) can advantageously but not limitingly be a column having the following specifications:

number of theoretical stages: from 10 to 85, preferably from 15 to 40, reflux ratio R of between 1 and 35, preferably between 5 and 25.

The distillation column (III) can very simply be a column of type (1) or alternatively a column having the following specifications:

number of theoretical stages: from 1 to 10, preferably from 1 to 5, reflux ratio R of between 0.5 and 5, preferably between 1 and 2.

The refining is carried out batchwise using devices which make possible liquid/solid separation (draining, zone melting) and which are dimensioned according to the volume to be treated and their number. The choice of the type of device is not critical either. They can, for example, be conventional drainers or other refining devices, for example those sold under the name Proapt (registered trademark). It is possible, for example, to use drainers of the type with a vertical cylindrical tubular exchanger.

The treatment of the rich fractions in these devices is carried out essentially according to the four following phases:

phase 1 corresponds to the slow crystallization of the charged mixture phase 2 corresponds to the cold draining of the eutectic (resorcinol and hydroquinone mixture)

phase 3 corresponds to the hot draining recovered during the reheating phase until the desired purity is obtained phase 4 corresponds to the melting-recovery of the pure product.

The production of fractions with substantially constant compositions also makes it possible to automate the progress of this refining.

The resorcinol-rich fraction is conveyed to one or more refining device(s). Before phase 1, the device is heated above the melting point of resorcinol (11° C.), i.e., for example, between 115 and 120° C.

During phase 1, the body of material is cooled, e.g. to a temperature of between 40 and 90° C., over several hours, e.g. over from 5 to 15 h, which results in the slow crystallization of the charged mixture.

After phase 1, the product which has remained liquid is withdrawn from the device (phase 2) before passing to phase 3.

Phase 3 consists of the slow reheating of the refining device, optionally begun during phase 2, e.g. up to a temperature of between 109 and 111° C., over several hours, e.g. over from 8 to 15 h. The end of phase 3, which conditions the purity of the product, can be determined either by measuring the crystallization point or by any other physiochemical analytical technique.

Phase 4 provides for heating of the device to a temperature greater than 115° C., so as to melt the resorcinol, which is withdrawn in the molten state.

The hydroquinone-rich fractions are treated in the same way. The treatment follows the same phases, apart from the heating/cooling temperatures and times. By way of example:

preheating between 175 and 180° C.

phase 1, cooling between 90 and 130° C.

phase 1, duration between 5 and 15 h phase 3, heating between 170 and 173° C.

phase 3, duration between 8 and 24 h phase 4, heating above 178° C.

The eutectic fractions recovered during the refining can be recycled as a mixture or separately with the hot drainings, preferably in stages (II) and/or (III). It is possible to be induced to recycle them in stage (I), if need be.

Another subject matter of the present invention is a plant which makes possible the implementation of the process described above, comprising:

(i) an optional distillation column (I) designed to produce catechol at the column top, (ii) a distillation column (II), the inlet of which is connected to the bottom of column (I) or receives the crude mixture in the absence of column (I), this column (II) being designed to produce, at the column top, a resorcinol-rich fraction comprising resorcinol, essentially, and hydroquinone, (iii) a distillation column (III), the inlet of which is connected to the bottom of column (II), this column (III) being designed to produce, at the column top, a hydroquinone-rich fraction comprising hydroquinone, essentially, and resorcinol, (iv) one or more refining devices (IV, V) for providing for the refining of the hydroquinone-rich fraction and/or the resorcinol-rich fraction in order to extract hydroquinone and/or resorcinol respectively.

In accordance with the preferred embodiment of the invention, this plant additionally comprises:

a detarring column (1) designed to produce, at the column top, a detarred fraction and, at the bottom of the column, a tar-rich fraction optionally at least one other distillation column (1') fed with the tar-rich fraction originating from the preceding column (1) and designed to produce, at the column top, a detarred fraction and, at the bottom, a tar-rich fraction, the top fraction or fractions of these columns being used to feed column (I) or (II).

The other information and characteristics given above with respect to the process apply directly to the plant according to the invention.

The invention will now be described in more detail with the help of embodiments taken as nonlimiting examples and with reference to the drawing, in which.

EXAMPLE 1

(FIG. 1)

Figure 1:
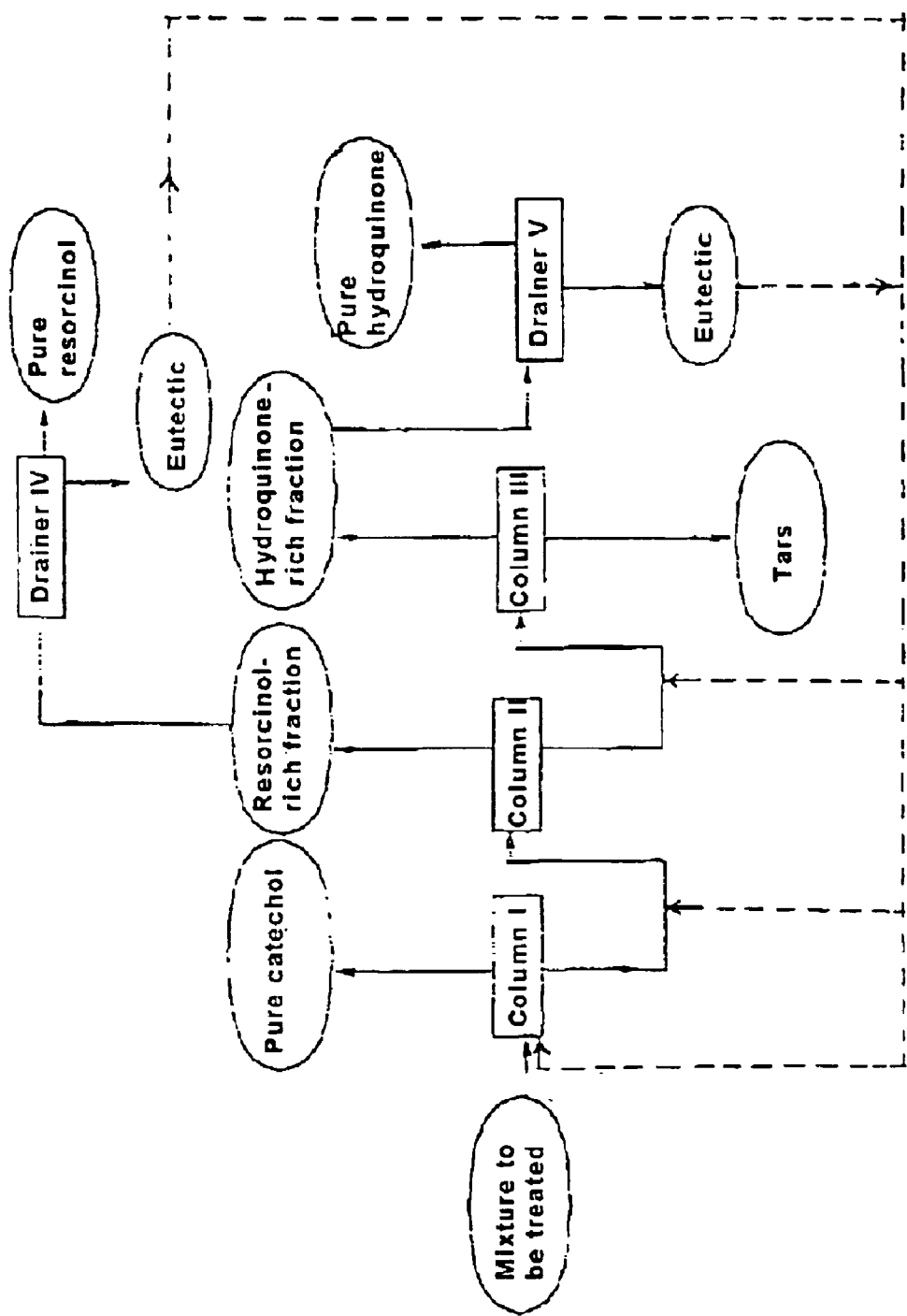
FIG. 1 shows the diagram of a first plant in accordance with the invention
Figure 2:
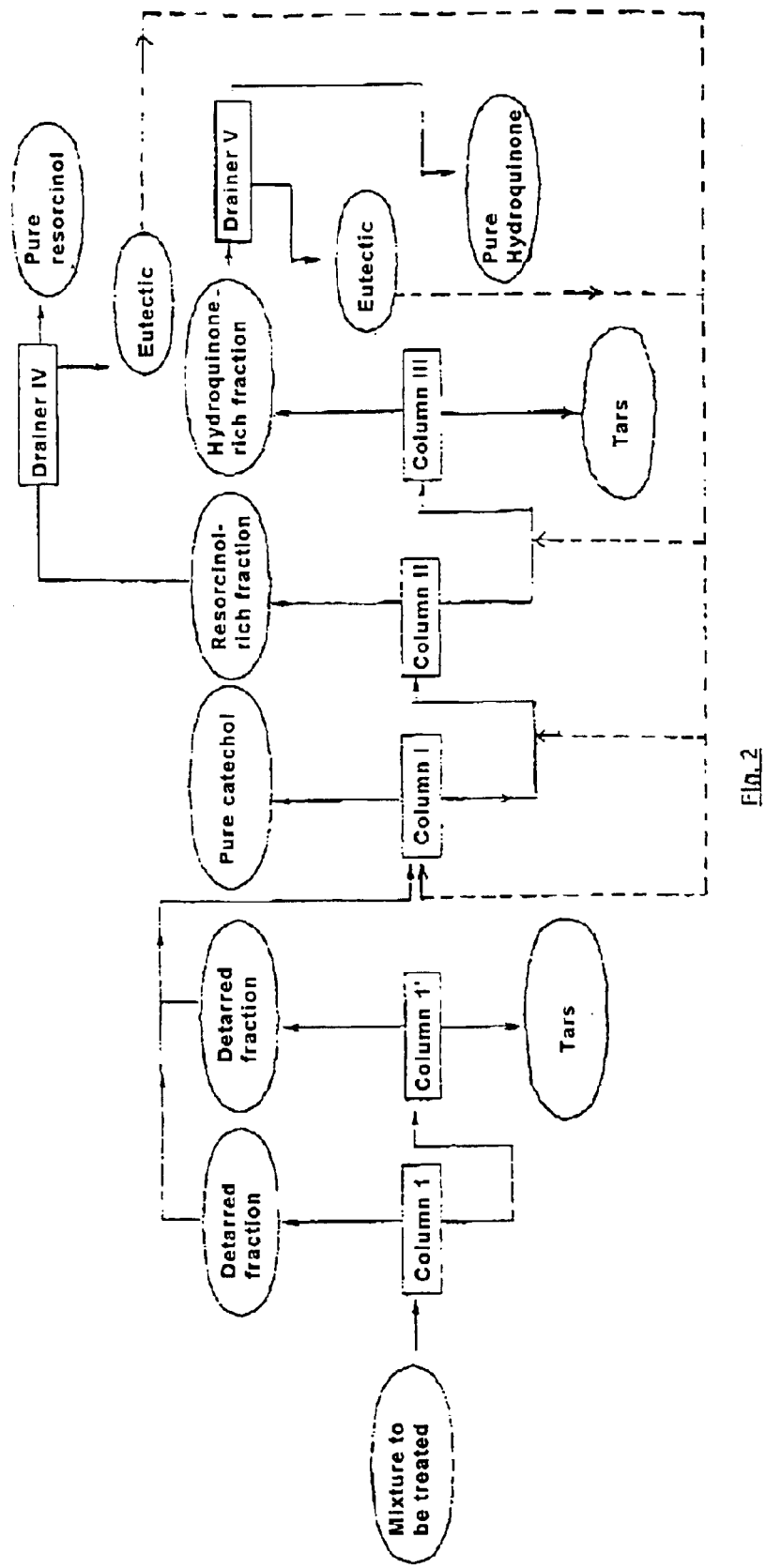
FIG. 2 shows the diagram of a second plant in accordance with the preferred embodiment of the invention.

1st Distillation Column (I);
n (number of theoretical stages)=30
R (reflux ratio)=2.7
Column top temperature=176.4° C.
Pressure=100 mmHg, i.e. 13 332 Pa.

This column (I) is fed continuously with a flow rate of 25.5 kg/h of a mixture to be treated comprising:
approximately 50% hydroquinone, i.e. approximately 12.75 kg/h
approximately 15% catechol, i.e. approximately 3.8 kg/h
approximately 10% resorcinol, i.e. approximately 2.55 kg/h
approximately 25% tars, i.e. approximately 6.4 kg/h.

A flow rate of approximately 3.8 kg/h is obtained at the column top, which flow rate comprises:
approximately 99.5% catechol
approximately 800 ppm hydroquinone
approximately 40 ppm resorcinol.

A flow rate of approximately 21.7 kg/h is obtained at the column bottom, which flow rate comprises:
approximately 58.9% hydroquinone (approximately 12.75 kg/h)
approximately 11.7% resorcinol (approximately 2.55 kg/h)
approximately 180 ppm catechol
approximately 29.4% tars (approximately 6.4 kg/h).

2nd Distillation Column (II):
n=30
R=10
Column top temperature: 210° C.
Pressure: =100 mmHg, i.e. 13 332 Pa.

It is fed continuously with the bottom product from the 1st column at a flow rate of approximately 21.7 kg/h.

A flow rate of approximately 2.56 kg/h of a resorcinol-rich fraction is obtained at the top, which fraction comprises:
approximately 90% resorcinol (approximately 2.3 kg/h)
approximately 10% hydroquinone (approximately, 0.26 kg/h,
approximately 1 200 ppm catechol.

A flow rate of approximately 19.14 kg/h of a mixture is obtained at the bottom, which mixture comprises:
approximately 65.3% hydroquinone (approximately 12.49 kg/h)
approximately 1.3% resorcinol (approximately 0.25 kg/h)
approximately 33.4% tars (approximately 6.4 kg/h).

3rd (Distillation) Detarring Column (III):
Detarring column: scraped falling film device
Column top temperature: 217° C.
Pressure: 100 mmHg, i.e. 13 332 Pa.

This column is fed continuously with the bottom product from the 2nd column at a flow rate of approximately 19.14 kg/h A flow rate of approximately 9.64 kg/h of a hydroquinone-rich fraction is obtained at the top, which fraction comprises:
approximately 97.4% hydroquinone (approximately 9.39 kg/h)
approximately 2.6% resorcinol (approximately 0.25 kg/h)

A flow rate of approximately 9.5 kg/h of a mixture is obtained at the column bottom, which mixture comprises:
approximately 32.6% hydroquinone (approximately 3.1 kg/h)
approximately 67.4% tars (approximately 6.4 kg/h).

The column bottom product can optionally be redistilled on a detarring column.

Refining:

The refining makes it possible to obtain the pure products from the rich fractions. Drainers of the type with a vertical cylindrical tubular exchanger were used. Similar results will be obtained with other types of devices.

The operating method is as follows:

a) for the hydroquinone-rich fraction:

Charging: before the charging of approximately 180 kg of hydroquinone-rich fractions, the drainer (V) is preheated to a temperature greater than the melting point of hydroquinone, in this instance to approximately 180° C.

Cooling: the body of material is slowly cooled by circulation of water to a temperature of approximately 120° C. (cooling time approximately 10 h).

Recovery of the eutectic fraction: the eutectic fraction, which is also known as cold drainings, corresponds to the uncrystallized part of the mixture at the end of cooling and is a mixture of resorcinol and hydroquinone. In the case of these drainers, this fraction can be recovered by simple gravimetric flow and collected in a tank provided for this purpose. This phase lasts approximately 12 hours and takes place with slow reheating of the drainer.

The reheating of the drainer is continued in order to carry out the hot draining phase. The end of the phase of recovery of the hot drainings is determined by the measurement of the crystallization point of the product which seeps out during this heating phase. This fraction is recovered by simple gravimetric flow and is collected in a tank provided for this purpose. This fraction can either be recycled to the following refining operation or mixed with the cold draining fraction and recycled to the distillation.

Recovery of the pure hydroquinone: when the crystallization point (171° C.) is reached, the flow of the hot drainings is interrupted and the drainer is heated to a temperature of 180° C. in order to melt all the hydroquinone. Approximately 65 kg of hydroquinone are recovered with an assay of greater than or equal to 99.5%.

b) For the resorcinol-rich fraction: the processing is carried out in the same way as under a) with the drainer (IV), apart from the essential difference that this time it is the melting temperature of resorcinol which is taken into account, which temperature is 111° C. The heating temperatures are consequently modified.

Charging temperature 120° C.
Cooling to 60° C. over approximately 10 h
Recovery of the cold draining fraction over approximately 10 h
Reheating from 60 to 110.5° C., the end of this reheating being determined by the measurement of the crystallization point, which determines the final purity of the product.
Heating to 120° C. in order to recover the resorcinol: 65 kg with a purity of greater than or equal to 99%.

EXAMPLE 2

(FIG. 2)

In comparison with example 1, two detarring columns (1 and 1') are added upstream of the distillation column (I) to remove at the start the tars present. The first (1) of these columns is fed with the mixture to be treated and the second (1') with the bottom product from the preceding column (1). The streams originating from the two column tops feed the 1st column (I) according to example 1.

Detarring Columns
Scraped falling film devices
Column top temperature: 174° C.
Pressure: 10 mmHg, i.e. 1 333.2 Pa.

The column (1) is fed continuously with a flow rate of 35 kg/h with a mixture to be treated comprising:
    approximately 45% hydroquinone, i.e. approximately 15.75 kg/h
    approximately 7% catechol, i.e. approximately 2.45 kg/h
    approximately 3% resorcinol, i.e. approximately 1.05 kg/h
    approximately 45% tars, i.e. approximately 15.75 kg/h.

The top products from the two detarring columns are combined and produce a flow rate of approximately 18.9 kg/h of a detarred fraction comprising:
    approximately 2.45 kg/h catechol
    approximately 15.3 kg/h hydroquinone
    approximately 1.05 kg/h resorcinol
    approximately 0.1 kg/h tars.

A flow rate of approximately 16.1 kg/h of a tar-rich fraction is obtained at the bottom of the column (1'), which fraction comprises:
    approximately 15.65 kg/h tars
    approximately 0.45 kg/h hydroquinone Distillation column (I):
n (number of theoretical stages)=30
R (reflux ratio)=2.7
Column top temperature=134° C.
Pressure=10 mmHg, i.e. 1 333.2 Pa.

This column (I) is fed continuously with the flow rate of 18.9 kg/h originating from the detarring.

A flow rate of approximately 2.45 kg/h is obtained at the column top, which flow rate comprises:
    approximately 99.5% catechol
    approximately 800 ppm hydroquinone
    approximately 40 ppm resorcinol.

A flow rate of approximately 16.45 kg/h is obtained at the column bottom, which flow rate comprises:
    approximately 15.3 kg/h hydroquinone
    approximately 1.05 kg/h resorcinol
    approximately 180 ppm catechol
    approximately 0.1 kg/h tars.

Distillation column (II):
n=30
R=10
Column top temperature: 170° C.
Pressure: 10 mmHg, i.e. 1 333.2 Pa.

It is fed continuously with the bottom product from the column (I) at a flow rate of approximately 16.45 kg/h.

A flow rate of approximately 0.75 kg/h of a resorcinol-rich fraction is obtained at the top, which fraction comprises:
    approximately 0.65 kg/h resorcinol
    approximately 0.1 kg/h hydroquinone
    approximately 1 200 ppm catechol.

A flow rate of approximately 15.7 kg/h of a mixture is obtained at the bottom, which mixture comprises:
    approximately 15.2 kg/h hydroquinone
    approximately 0.4 kg/h resorcinol
    approximately 0.1 kg/h tars.

(Distillation) detarring column (III):
Detarring column: scraped falling film device
Column top temperature: 174.5° C.
Pressure: 10 mmHg, i.e. 1 333.2 Pa.

This column is fed continuously with the bottom product from the column (II) at a flow rate of approximately 15.7 kg/h.

A flow rate of approximately 15.2 kg/h of a hydroquinone-rich fraction is obtained at the top, which fraction comprises:
    approximately 14.8 kg/h hydroquinone
    approximately 0.4 kg/h resorcinol.

A flow rate of approximately 0.5 kg/h of a mixture is obtained at the column bottom, which mixture comprises:
    approximately 0.4 kg/h hydroquinone approximately 0.1 kg/h tars.

Refining:
The refining is carried out as in example 1.

It must be clearly understood that the invention defined by the appended claims is not limited to the specific embodiments indicated in the above description but encompasses the alternative forms thereof which depart neither from the scope nor from the spirit of the present invention.

What is claimed is:

1. A process for separation and purification of a crude mixture comprising hydroquinone and resorcinol, in which process the crude mixture is first subjected to a series of distillation stages comprising:
    (i) subjecting the crude mixture to a distillation stage (II) designed to produce, as a distillation top product, a resorcinol-rich fraction comprising resorcinol, essentially, and hydroquinone;
    (ii) subjecting a distillation bottom product obtained by step (i) to a distillation stage (III) designed to produce, as a distillation top product, a hydroquinone-rich fraction comprising hydroquinone, essentially, and resorcinol;

and then subjecting the hydroquinone-rich fraction and/or the resorcinol-rich fraction to a refining stage (IV or V) in order to extract the hydroquinone and/or the resorcinol, respectively, wherein the refining stage comprises successive cooling/crystallization, draining of a eutectic, reheating and draining a liquid fraction, and then melting-recovering a crystallized fraction.

2. The process according to claim 1, wherein the hydroquinone-rich fraction obtained by distillation stage (III) is submitted to a refining stage comprising the following successive phases:

phase 1: slow cooling of the fraction for 5 to 15 h until a temperature of between 90 and 130° C. is reached;

phase 2: draining the liquid fraction;

phase 3: slow reheating for 8 to 24 h until a temperature of between 170 and 173° C. is reached, and draining the liquid fraction; and phase 4: heating to 178° C. and recovering hydroquinone.

3. The process according to 2, wherein, before phase 1, the hydroquinone-rich fraction is heated above the melting point of hydroquinone.

4. The process according to 3, wherein, before phase 1, the hydroquinone-rich fraction is heated to a temperature between 175 and 180° C.

5. The process according to claim 3 or 4, wherein phase 3 is stopped when the temperature reaches 171° C.

6. The process according to any one of claims 1 to 4, wherein stages (II) and (III) are performed so as to obtain at the top of stage (III) a hydroquinone-rich fraction comprising from 75 to 98% of hydroquinone and from 2 to 25% of resorcinol, these percentages being expressed with respect to the sum of hydroquinone and resorcinol.

7. The process according to claim 6, wherein said hydroquinone-rich fraction comprises 85 to 97.5% of hydroquinone and 2.5 to 15% of resorcinol.

8. The process according to claim 1, wherein the resorcinol-rich fraction obtained at the top of stage (II) is submitted to a refining stage comprising the following successive phases:

phase 1: slow cooling of the fraction for 5 to 15 h until a temperature of between 40 and 90° C. is reached;

phase 2: draining the liquid fraction;

phase 3: slow reheating for 8 to 15 h until a temperature of between 109 and 111° C. is reached, and draining the liquid fraction; and phase 4: heating to 115° C. and recovering hydroquinone.

9. The process according to claim 8, wherein, before phase 1, the resorcinol-rich fraction is heated above the melting point of resorcinol.

10. The process according to claim 9, wherein, before phase 1, the resorcinol-rich fraction is heated to a temperature between 115 and 120° C.

11. The process according to claim 8 or 10, wherein phase 3 is stopped when the temperature reaches 111° C.

12. The process according to any one of claims 8 to 10 wherein stage (III) is performed so as to obtain at the top of stage (II) a resorcinol-rich fraction comprising from 75 to 98% of resorcinol and from 2 to 25% of hydroquinone, these percentages being expressed with respect to the sum of hydroquinone and resorcinol.

13. The process according to claim 12, wherein said resorcinol-rich fraction comprises 85 to 92% of resorcinol and 8 to 15% of hydroquinone.

14. The process according to claim 1, wherein refining of the rich fractions is conducted on a drainer.

15. The process according to claim 1, wherein the crude mixture further comprises catechol and stage (II) is preceded by a distillation stage (I) designed to produce catechol as distillation top product, and the distillation bottom product is used to feed stage (II).

16. The process as claimed in claim 15, wherein stage (I), when it is present, or stage (II) is preceded by at least one predistillation stage (1,1') designed to produce, as bottom product, a tar-rich fraction and, as top product, a detarred fraction which is used to feed stage (I) or stage (II).

17. The process as claimed in claim 16, wherein two predistillation stages (1,1') are provided, the tar-rich bottom fraction from the first predistillation stage (1) being used to feed the second predistillation stage (1') and wherein the two detarred top fractions are used to feed stage (I) or (II).

18. The process as claimed in claim 15, wherein the distillation column for distillation stage (I) has from 5 to 40 theoretical stages; and a reflux ratio R of between 1 and 10.

19. The process as claimed in claim 18, wherein the distillation column has 10 to 30 theoretical stages.

20. The process as claimed in claim 18, wherein the reflux ratio R is between 2 and 5.

21. The process as claimed in claim 1, wherein the distillation column for distillation stage (II) has from 10 to 85 theoretical stages; and a reflux ratio R of between 1 and 35.

22. The process as claimed in claim 21, wherein the distillation column has 15 to 40 theoretical stages.

23. The process as claimed in claim 21, wherein the reflux ratio R is between 5 and 25.

24. The process as claimed in claim 1, wherein the distillation column for distillation stage (III) is a scraped falling film device or a distillation column having from 1 to 10 theoretical stages; and a reflux ratio R of between 0.5 and 5.

25. The process as claimed in claim 24, wherein when the column is a distillation column, the column has 1 to 5 theoretical stages.

26. The process as claimed in claim 24, wherein when the column is a distillation column, the reflux ratio R is between 1 and 2.

27. The process as claimed in claim 16 or 17, wherein the column or columns for the predistillation stage (1,1') is/are scraped falling film devices.

28. The process as claimed in claim 1, wherein the crude mixture comprises, with respect to the total mixture:

from 20 to 60% by weight of hydroquinone;

from 2 to 20% by weight of resorcinol;

from 0 to 20% by weight of catechol; and the remainder being formed of various compounds, essentially tars.

29. The process as claimed in claim 28, wherein the mixture comprises 30–50% by weight of hydroquinone.

30. The process as claimed in claim 28, wherein the mixture comprises 2 to 15% by weight of resorcinol.

31. The process as claimed in claim 28, wherein the mixture comprises 5 to 15% by weight of catechol.

* * * * *